United States Patent
Belly et al.

[11] Patent Number: 5,958,339
[45] Date of Patent: Sep. 28, 1999

[54] FORMAT FOR IMMUNOASSAY IN THIN FILM

[75] Inventors: Robert Troconis Belly, Webster; Martha Miller Kopcienski, Spencerport; Caroline Erdrich, Fairport; Maurice A. Kildal, Webster, all of N.Y.

[73] Assignee: Clinical Diagnostic Systems, Inc., Rochester, N.Y.

[21] Appl. No.: 07/938,460

[22] Filed: Aug. 31, 1992

[51] Int. Cl.$^6$ ................................ G01N 31/22
[52] U.S. Cl. ................................ 422/56; 422/58
[58] Field of Search .................. 422/56, 57, 58, 422/60; 436/515, 518, 810, 800

[56] References Cited

U.S. PATENT DOCUMENTS

| | | | |
|---|---|---|---|
| 3,876,504 | 4/1975 | Koffler | 195/103.5 |
| 4,258,001 | 3/1981 | Pierce et al. | 422/56 |
| 4,292,272 | 9/1981 | Kitajima et al. | 422/57 |
| 4,517,288 | 5/1985 | Giegel et al. | 435/5 |
| 4,738,823 | 4/1988 | Engelman | 422/56 |
| 4,740,468 | 4/1988 | Weng et al. | 435/7 |
| 4,752,562 | 6/1988 | Sheiman et al. | 435/5 |
| 4,774,174 | 9/1988 | Giegel et al. | 435/5 |
| 4,806,312 | 2/1989 | Greenquist | 422/56 |
| 4,828,983 | 5/1989 | McClune et al. | 435/7.92 |
| 4,857,453 | 8/1989 | Ullman et al. | 435/7 |
| 4,861,711 | 8/1989 | Friesen et al. | 436/7 |
| 4,886,761 | 12/1989 | Gustafson et al. | 436/518 |
| 4,891,313 | 1/1990 | Berger et al. | 435/7.94 |
| 4,959,305 | 9/1990 | Woodrum | 435/7 |
| 4,981,786 | 1/1991 | Dafforn et al. | 435/7 |
| 5,006,474 | 4/1991 | Horstman et al. | 436/524 |
| 5,028,528 | 7/1991 | Frickey et al. | 435/21 |
| 5,122,451 | 6/1992 | Tanaka et al. | 435/74 |

FOREIGN PATENT DOCUMENTS

| | | |
|---|---|---|
| 60-173471 | 9/1985 | Japan. |
| 61-062864 | 3/1986 | Japan. |
| 61-062865 | 3/1986 | Japan. |
| 61-126470 | 6/1986 | Japan. |
| 61-126471 | 6/1986 | Japan. |

OTHER PUBLICATIONS

United States Statutory Invention Registration Reg. No. 14791, Katsuyama et al., Jun. 5, 1990.

*Primary Examiner*—Jill Warden

[57] ABSTRACT

The present invention provides a novel dry analytical element for determination of an analyte in a fluid sample in thin film immunoassay, particularly chemiluminescence, fluorescence and colorimetry immunoassay. There is provided an analytical element comprising a support member, a reagent matrix comprised of at least one layer of a porous material carried on the support member, the matrix including a read area, an absorbent material in contact with the matrix, and light absorbing or reflecting means integral to the absorbent material and/or positioned between the absorbant material and the read area for absorbing or blocking background signal generated by washed, removed label and other interferents from outside the read area prior to it moving back into the read area. The analytical element can comprises a cover depending on the type of immunoassay to be conducted.

12 Claims, 7 Drawing Sheets

FORMAT FOR IMMUNOASSAY IN THIN FILM

FIELD OF THE INVENTION

The present invention relates to a dry analytical element for use in thin film immunoassay and, more particularly, to an element having increased wash volume capacity and means for minimizing background due to washed, removed label and other interferents from outside the read area.

BACKGROUND OF THE INVENTION

Immunoassay is a well-recognized technique for qualitative or quantitative assay of antibodies and antigens. The basis for all immunoassay techniques is the unique, immunological phenomena whereby a specific antibody recognizes and binds to a specific antigen. Immunochemical techniques offer advantages in terms of assay sensitivity because of the high affinity of antibody for its specific antigen. Therefore, in many instances immunoassay has made possible the detection of biological compounds that are present in trace quantities too low for traditional chemical and enzymatic techniques.

In general, immunoassay techniques can provide for a determination of the presence and/or concentration of either a specific antigen, a specific antibody, or a specific antigen-antibody complex. For example, given a known amount of antibody (or antigen), the level of its corresponding antigen (or antibody), sometimes referred to as its complement, can be determined. When the concentration of antigen (or antibody) is too small for direct measurement, a label (i.e. detectable species as described hereinafter) can be affixed to a known fraction of the antigen (or antibody). This label, which is present and measurable at the requisite concentration, acts as a marker for the extent of antibody/antigen binding between the unknown antigen (or antibody) and its antibody (or antigen). The distribution of label between the bound and unbound antigen (or antibody) can then be used to calculate the amount of unknown that was present in liquid test sample.

In an alternative type of immunological assay, commonly referred to as a sandwich assay, an antibody and/or antigen is contacted with a sample containing an analyte to cause the analyte to bind to the antibody. This complex is then contacted with a solution of a labeled antibody and/or antigen which reacts with the bound analyte. The amount of bound labeled antibody and/or antigen is thus directly proportional to the amount of bound analyte.

Current immunoassay techniques in dry analytical elements are aimed at detection of serum components present in the test sample only in nanomolar concentrations. For detection of many diagnostically important serum hormones and cancer markers, detection at picomolar concentrations are required. Among the medically important hormones present in serum at picomolar concentration are aldosterone, insulin, TSH, angiotensin, ocytocin, parathyroid hormone (PTH), growth hormone, ACTH, and vasopressin. To perform immunoassay for serum analytes present at picomolar concentration, a sensitive detection chemistry such as fluorescence or chemiluminescence is needed. Because of the sensitivity of this type of detection chemistry, background due to unbound label or chemical interferents present in the serum sample have to be thoroughly removed. This is accomplished by an exhaustive wash step after the binding reaction of antibody with antigen has occurred. However, the fluid capacity of current thin film formats, typically a wash volume capacity of about 10 to 20 $\mu$L, is not sufficient to permit immunoassay of analytes at concentrations much below 1 nanomolar.

For example, U.S. Pat. No. 4,752,562 to Sheiman et al, discloses a radial partition immunoassay wherein typical solvent (wash) volumes range from 10 to 150 $\mu$L. However, this type of element is not suitable for use in thin film immunoassay.

U.S. Pat. No. 4,738,823 to Helmut Engelmann, discloses a test strip with adjustable sample absorption capacity. The test strip comprises a support or carrier having an adjustable depression. A reagent strip and absorbent material are fixed in and at the edges of the depression, respectively. Adjusting the depth of the depression determines the volume of sample which can be applied to the reagent strip. The absorbent, however, is positioned to remove excess sample applied, not wash.

Japanese Kokai Patent Application No. Sho 61[1986]-126471 discloses a dry-type element for detection of antigen with a catalytic effect for a specific reaction, with improved washing effect for substances other than the target antigen. The material that absorbs the washing solution is arranged on the periphery of, or as an overlapped layer on, the antibody-fixed layer. However, a cumbersome two-step process is required where first a wash solution is applied to separate interferences present in the serum and then a solution containing the detection chemistry is applied. Furthermore, the washing solution is applied in several 50 $\mu$L volume increments.

Furthermore, another problem associated with using conventional dry analytical elements in chemiluminescent or fluorescent immunoassay is that of light piping. Light piping occurs when signal from removed (washed) label moves back into the read area. This phenomena substantially decreases the sensitivity reading of the assay.

Therefore, a need exists for a dry analytical element for thin film immunoassay for the detection of low level analytes from fluid samples by means of chemiluminescence, fluorescence or colorimetry.

OBJECT AND SUMMARY OF THE INVENTION

The object of the present invention is to provide a dry analytical element having increased wash volume capacity, for use in thin film immunoassays for determination of an analyte present in a fluid sample.

The present invention provides a novel dry analytical element for quantitative analysis of a fluid sample in thin film immunoassay, particularly chemiluminescence, fluorescence or colorimetry immunoassay. There is provided an analytical element comprising a support member; a reagent matrix comprised of at least one layer of a porous material carried on the support member, the matrix including a read area; an absorbent material in contact with the matrix; and light absorbing or reflecting means integral to the absorbent material and/or positioned between the absorbent material and the read area for absorbing or blocking background signal generated by washed, removed label and other interferents from outside the read area from moving back into read area. The analytical element optionally can comprise a top or cover depending on the type of immunoassay to be conducted.

The analytical element of the invention provides increased wash volume capacity of up to about 1 mL, when compared to current elements. Further, the present element provides light absorbing or reflecting means for absorbing or blocking background due to washed, removed label. As a result, background due to unbound label and interfering serum components is substantially decreased, as required for immunoassay of low level analytes.

In one illustrative embodiment, in performing an immunoassay using the analytical element of the invention, a sample of serum or other fluid is spotted on the reagent matrix. After an incubation period, allowing for the chemical reaction to occur (i.e., competitive or sandwich assay), the read area of the reagent matrix, which is to be monitored for analyte concentration, is washed with up to about 250 $\mu$L of wash solution, preferably at a metered rate of up to 10 $\mu$L/sec, and most preferably 1 $\mu$L/sec. It is preferred that the detection solution be used as the wash solution. However, the signal-generating substrate can be added as a separate fluid after the wash step. Upon wetting, the absorbent material of the element absorbs the wash fluid containing soluble interferents and unbound label away from the read area of the reagent matrix, thereby decreasing background interference from the read area. Further, the light absorbing or reflecting means associated with the absorbent material absorbs or blocks background signal generated by washed, removed label and other interferents from outside the read area, thereby preventing the background from moving back into the read area. This increases efficiency and sensitivity of the immunoassay. Thereafter, the detection signal (i.e., chemiluminescence, fluorescence or colorimetry) is measured to determine analyte concentration.

DETAILED DESCRIPTION OF THE INVENTION

The present invention provides a novel dry analytical element for the determination of a chemical or biological substance termed an "analyte" herein, in aqueous liquids in thin film immunoassay. The term "determination" as used herein, refers to either the qualitative or quantitative measurement of the analyte. In particular, the invention can be used to assay biological fluids of either animals or humans including, but not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like, serum hormones, drugs, enzymes and cancer markers as well as microorganisms and antibodies to such organisms. Likewise, immunoassays can be used in foods, environmental fluids, or for any diagnostics based on immunoassays.

The analytical element of the invention comprises an improved wash volume capacity of up to about 1 mL. Thus pseudopositive or pseudonegative results for detection of low level analytes are minimized. As used herein, the terms "read area" and "reaction zone" are interchangeable and refer to that portion of the element which is to be monitored for analyte concentration.

Figure 1:
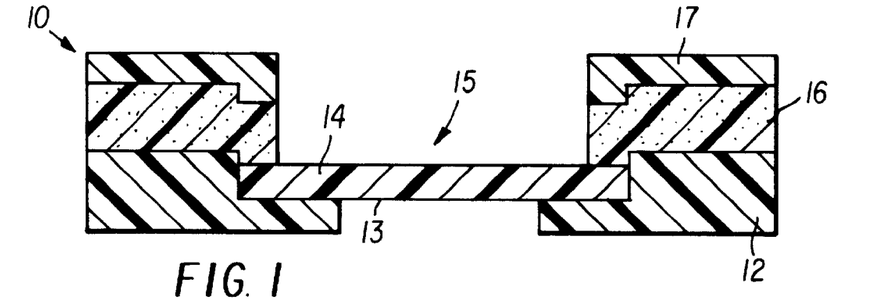
FIG. 1 is a cross-sectional view of one embodiment of the analytical element of the present invention.
Figure 2:
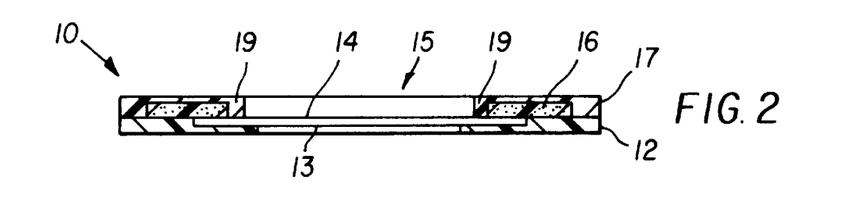
FIG. 2 is a cross-sectional view of an alternative embodiment of the analytical element of the present invention.

With reference to FIGS. 1 and 2, there is shown, generally at 10, illustrative embodiments of the dry analytical element of the present invention. The analytical element comprises a base 12, a reagent matrix 14 carried on support member 13 and having a read area 15, an absorbent material 16 in contact with matrix 14, in one embodiment is positioned adjacent to at least a portion of the periphery of read area 15 and light absorbing or reflecting means in contact with the absorbent material. The light absorbing or reflecting means can be a separate unit positioned between absorbent material 16 and read area 15, as shown by flange 19 in FIG. 2. Alternatively, light absorbing or reflecting means can be comprised as an integral part of at least a portion of the absorbent material, as shown in FIG. 1. Optionally, a cover 17 can be positioned above absorbent material 16. Using the novel analytical element, it has been made possible to substantially increase wash volume for performing thin film immunoassays. This increases the sensitivity of the assay by removing unbound label and soluble interferents from the read area.

In a preferred embodiment, reagent matrix 14 of analytical element 10 comprises at least one porous spreading zone or layer, containing an immobilized binding agent capable of reacting with the analyte of interest and a label (e.g., supplied in any known manner) which is capable of either competing with the analyte for binding sites on the binding agent coated therein or binding with a binding agent-analyte complex, forming an immunosandwich. It is desirable that the spreading zone be isotropically porous, meaning that the porosity is the same in each direction in the zone as caused by interconnected spaces or pores between particles, fibers or polymeric strands. The porosity of the matrix can be sufficiently fine to entrap the analyte thereby effectively immobilizing it within its interstices. Alternatively, where the physical size of the analyte of interest is too small for effective physical entrapment, and therefore immobilizing the analyte within the inert matrix, the matrix can be sensitized with an appropriate agent (i.e., antibody) to bind such finer particles.

The spreading zone can have two or more discrete zones, either in the same layer or as superimposed layers. The zones can be reagent zones, capture zones or registration zones as those zones are known in the art, additional spreading zones, radiation-blocking or filter zones, subbing zones, gel zones, barrier zones, etc. The zones are generally in fluid contact with each other, meaning that fluids, reagents and reaction products (e.g., color dyes) can pass or be transported between superposed regions of adjacent zones. Preferably, the zones are separately coated layers, although two or more zones can be a single layer.

The zones can be self supporting (i.e., composed of a material rigid enough to maintain its integrity), but preferably are carried on a separate support member 13. Support 13 can be any suitable dimensionally stable, and preferably, nonporous and transparent (i.e., radiation transmissive) material which transmits electromagnetic radiation of a wavelength between about 200 and about 900 nm. A support of choice for a particular matrix should be compatible with the intended mode of detection (i.e., transmission or reflectance spectroscopy). Useful supports can be prepared from paper, metal foils, polystyrene, polyesters [e.g., poly (ethylene terephthalate)], polycarbonates, cellulose esters (e.g., cellulose acetate) and others known in the art. Top or cover 17 and base 12 are comprised of a similar or the same material as support 13. For example, any plastic polymer including thermal plastic polymers such as polyolefins and copolymers of olefins, and preferably, polystyrene, polyethylene, polypropylene and the latter copolymerized with ethylene vinyl acetate. Base and/or top profiles can, however, also be produced by combining several of the above materials. The base, top, and/or analytical element can be bonded to one another, for example, by adhesive, tape or ultrasonics.

The support, however, also is typically a subbed, gel-washed poly(ethylene terephthalate) support before at least one of the zones previously described is coated thereon. The initial sub on the support is preferably a vinylidene chloride copolymer as is typically used on photographic supports in the art and disclosed in U.S. Pat. Nos. 3,143,421; 3,271,345 and 2,943,937, which disclosures are hereby incorporated by reference.

The porous spreading zone can be prepared from any suitable fibrous or non-fibrous material or mixtures of either or both. The void volume and average pore size of this zone can be varied depending upon the use intended. Useful spreading zones can be prepared using fibrous materials, either mixed with a suitable binder material or woven into a fabric, as described in U.S. Pat. No. 4,292,272 (issued Sep. 29, 1981 to Kitajima et al.), which disclosure is hereby incorporated by reference. Alternatively, and preferably, the spreading zone is prepared from polymeric compositions (for example, blush polymers) or particulate materials, as described in U.S. Pat. Nos. 3,992,158 (issued Nov. 16, 1976 to Przybylowicz et al.), 4,258,001 (issued Mar. 24, 1981 to Pierce et al.), and 4,430,436 (issued Feb. 7, 1984 to Koyama et al.) and Japanese Patent Publication 57 (1982)-101760 (published Jun. 24, 1982), which disclosures are hereby incorporated by reference.

A water-insoluble adhesive can be employed to bond the organo-polymeric particles to one another to provide the coherent, three-dimensional structure of the spreading zone. The adhesive is composed of an organic polymer different from the specific polymer contained in the spreading zone, although quite commonly the adhesive represents a polymer containing many repeating units which are identical or similar to some of those present in the polymer composition of the spreading zone. Preferred water-insoluble adhesives for use in the invention are addition homopolymers and copolymers, particularly addition copolymers prepared from an addition polymerizable blend of monomers, although any known adhesive in the art may be used herein. For example, reference is made to U.S. Pat. No. 4,258,001, which disclosure is hereby incorporated by reference.

A leuco dye can also be incorporated into the spreading zone and/or other zones. Any suitable leuco dye can be used in the practice of this invention as long as it is capable of providing a detectable dye when oxidized in the presence of the label. Examples of useful leuco dyes include, but are not limited to, imidazole derivatives such as those described in U.S. Pat. No. 4,089,747 and references noted therein, European Patent Application No. 122,641 (published Oct. 24, 1984) and Japanese Patent Publication No. 58(1983)-045,557, and the triarylmethanes described, for example, in U.S Pat. No. 4,670,385, which disclosures are hereby incorporated by reference. Likewise, any fluoresecnt or chemiluminescene generating material can be used herein.

A buffering agent can also be incorporated into the spreading zone and/or other zones. The buffering agent maintains the pH of the assay at 9.0 or less, and preferably from about 6.0 to about 9.0. Any suitable buffering agent or mixture of buffers can be used herein as long as the buffer is capable of maintaining the pH during the assay at about 9.0 or less. Particularly preferred buffers include, but are not limited to, tris(hydroxymethyl)aminoethane hydrochloride, glycylglycine, N-[tris(hydroxymethyl)methyl]-2-aminoethanesulfonic acid (TES), N-(2-hydroxyethyl)-piperazine-N'-2-ethanesulfonic acid, N-[tris(hydroxymethyl)methyl]-2-aminoethanesulfonic acid being most preferred, although any buffer standard in the art may be used. For example, see Good et al., Biochem, 5(2), 1966, pp. 467–477. The buffer is present in a suitable amount, depending on the particular buffer, which can easily be determined by one of ordinary skill in clinical chemistry.

An electron transfer agent can also be incorporated into the spreading zone and/or other zones. Phenols or anilines, which act as electron transfer agents are preferred although any electron transfer agent known in the art can be used herein. Representative phenols useful in this invention include: p,p'-biphenol, 4'-hydroxyacetanilide (4'-HA), p-methoxyphenol, chlorphenol red, p-cresol, m-methoxyphenol, vanillin, 4-chloro-3,5-bis (dimethylamino)phenol, homovanillic acid, p-hydroxybenzoic acid, p-hydroxyphenylacetic acid, o-methoxyphenol, phenol, resorcinol and methyl p-hydroxybenzoate. Useful anilines include: p-anisidine, 4'-aminoacetanilide, p-hydroxy-N,N-dimethylaniline and o-phenylenediamine. Phenols and anilines selected from the group consisting of p,p'-biphenol, 4'-hydroxyacetanilide, p-methoxyphenol, p-anisidine and 4'-aminoacetanilide are more preferred, and 4'-hydroxyacetanilide is most preferred. The electron transfer agent is present in a suitable amount, depending on the particular agent, which can easily be determined by one of ordinary skill in clinical chemistry.

In a preferred embodiment, the analytical element of the present invention is useful for the determination of an immunologically reactive ligand, which is a substance that will complex specifically with a corresponding reactant. As used herein, the term "ligand" is interchangeable with analyte. Such ligands include, but are not limited to, antigens, haptens, antibodies, toxins, hormones, therapeutic drugs, natural and synthetic steroids, proteins, viruses, bacteria, peptides, nucleotides, etc. The ligand (analyte) to be determined and corresponding labeled ligand analog compete for, or form a sandwich with, a fixed amount of binding agent.

The ligand analog can comprise a ligand covalently bonded to a suitable label. The purpose of the label is to provide an indirect means for measuring the amount of analyte present in the sample. The labeled compound is designed to immunochemically bind to the analyte entrapped within the matrix. The synthesis of labeled compounds suitable for use in the method of this invention can be performed by well-known synthetic protocols. Labeled ligand analogs useful in this invention can be prepared using any signal generating label and suitable technique known to one skilled in the art. For example, conventional labels include enzymes such as peroxidase, e.g., horseradish peroxidase, an enzyme other than peroxidase such as glucose oxidase, alkaline phosphatase, galactose oxidase, and the like, radioactive tags, chromophores, fluorophores, and enzyme cofactors and effectors. Enzymes can be measured by reacting the labeled ligand with a substrate, which by the action of the enzyme, releases a chromogenic or fluorogenic substance that can be measured by conventional techniques or that activates a chemiluminescence substance which gives off light with an intensity proportional to the analyte concentration. Ligands labeled with enzyme cofactors or effectors can be detected similarly by their effect on enzyme action on a substrate. Compounds labeled with chromophores, fluorescent and chemiluminescent compounds can be directly measurable, e.g. by fluorescence, ultraviolet spectroscopy or other spectroscopic means. For illustrative purposes, the preferred detection chemistry is enhanced chemiluminescence according to the following reaction:

where ETA (electron transfer agent) is an aniline or phenol such as 4'-Hydroxyacetanilide (4'-HA) and HRP is horseradish peroxidase.

The labeled ligand analog and corresponding binding agent which specifically recognizes the ligand to be assayed can be incorporated into the spreading zone prior to use, or added at the time of the assay. Preferably, both are incorporated into the spreading zone prior to use. More particularly, the binding agent can be immobilized within the porous spreading zone on a carrier material, such as glass or polymeric beads or other particles, resins, fibers and the like. Alternatively, the binding agent can be incorporated into an intermediate layer or zone separate from the spreading zone. Additionally, the labeled ligand analog can be incorporated into a separate water-soluble zone or layer in order to isolate it from the reactant.

The binding agent immobilized in the spreading zone or alternative intermediate layer or zone can comprise any known binding agent in the art, for example, phosphorylcholine, avidin, biotin, thyroxin, thyroxin binding globulin, a polysaccharide etc., an antigen, an antibody, an estrogen receptor or any other receptor selected to specifically bind and capture the analyte (ligand) of interest. To serve as a capture agent, the binding agent is immobilized by absorption or covalent binding to an insoluble carrier such as glass or polymer beads or other particles, resins, fibers or the like.

The reagent matrix can be configured in a variety of forms, including elongated tapes of any desired width, sheets, slides or preferably chips. Further, the assay can be manual or automated. In general, in using the analytical element of the invention, analyte (ligand) determination is made by taking the reagent matrix from a supply roll, chip packet or other source, placing it into a slide mount format i.e., base, cover and adsorbent/light absorbing material and physically contacting it with a sample (e.g., 1–200 $\mu$l, preferably 10 $\mu$l) of the liquid suspected of containing the analyte so that the sample and reagents within the matrix become mixed. Such contact can be accomplished in any suitable manner, e.g., preferably, by spotting the element by hand or machine with a drop of the sample using a suitable dispensing means.

After sample application, the element is exposed to any conditioning, such as incubation, heating or the like, that may be desirable to quicken or otherwise facilitate obtaining any test result to form a complex between the ligand and ligand analog and the binding agent. A clean separation of unbound label compounds, as well as interfering serum components, must then be removed from the read area (reaction zone) prior to the monitoring step. This separation can be accomplished by applying a stream of a washing solution to the reaction zone in sufficient volume to separate unbound materials from the reaction zone. Preferably, the wash solution is applied at a continuous metered rate, for example, of up to 10 $\mu$L/sec, and most preferably 1 $\mu$L/sec, although, intermittent application can be used. It is understood that as long as no "puddles" form on the spreading layer of the assay that any method of application and rate can be employed, so long as the rate of application is about equal to the rate of wash fluid absorption into the spreading layer. However, if puddling does occur, a water-impermeable material can be placed around the area immediately adjacent the read area which is further described herinafter. As the solvent (wash fluid) migrates outward from its point of application, unbound reactants are dissolved therein and separate from the bound reactants.

The wash solution can comprise any known solution in the art used for washing, such as distilled water or a buffer solution in which such unbound compounds are conveniently dissolved, and in some embodiments is preferably a buffer solution including a buffering agent and optionally an electron transfer agent, peroxide, chelating agent and/or surfactant. Preferably, the wash solution contains the detection (label) chemistry which eliminates the additional step of adding a separate wash solution.

Figure 3:
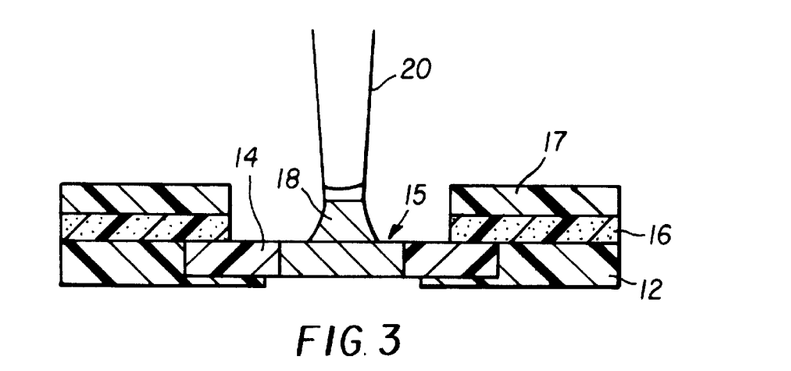
FIGS. 3. and 4 are cross-sectional views of the element of the present invention having wash solution applied thereto.

Current thin film immunoassays typically have a wash volume capacity of from about 10 to 20 $\mu$L. One novel aspect of the element of the invention is that it has increased wash volume capacity of upwards to about 1 mL, depending on the thickness of the element. This is significant because a large wash volume separates out substantially all unbound label and serum components from the read area, thereby providing a more sensitive immunoassay. With reference to FIG. 3, wash volume 18 (indicated by diagonal lines) may be conveniently applied to reaction zone 15 with a pipette, hypodermic syringe or other dispensing device 20. It is understood that the volume of fluids applied to the matrix in the performance of the assay for this invention is sufficient to effect an essentially homogeneous area within the reaction zone for monitoring of the analyte of interest. This is accomplished because the absorbent material in the element permits retention of all of such fluid entirely within the material.

Figure 4:
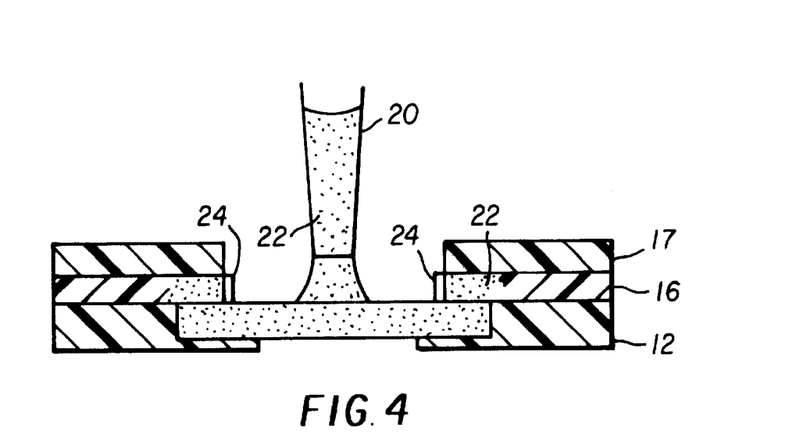

As shown in FIG. 4, absorbent material 16 takes up (absorbs) wash fluid 22, which contains soluble interferents and unbound label, away from read area 15. With reference to FIGS. 1 and 2, absorbent material 16, is positioned in contact with matrix 14, and, in one embodiment, adjacent to at least a portion of the periphery of read area 15. It is understood that for "off-center" wash immunoassay, the absorbent material will be positioned on the matrix adjacent to the position of wash application. Absorbent material 16 can be comprised of materials such as glass microfibers, paper, sponge, fabric, plastic or the like, so long as the material is capable of absorbing liquids. The ability to absorb liquid may be influenced by pretreating the absorbent material, for example, with additional absorbent enhancing agents such as wetting agents or the introduction of functional groups. Optionally, the absorbent can be sealed with paraffin or other water-impermeable material (24 at FIG. 4) around the area immediately adjacent the read area. This may increase wash efficiency by not allowing fluid to be absorbed prior to permiation through the matrix.

The element further comprises light absorbing or reflecting means which can comprise a separate unit positioned between the absorbent material and the read area or formed integral to at least a portion of the absorbent material. With reference to FIG. 1, light absorbing or reflecting means comprises a light absorbing or reflecting material which is integral to at least a portion of the absorbent material. That is, the absorbent material can be entirely comprised of the light absorbing or reflecting material or color, for example, such as black or pigmented polyvinyl alcohol, black or pigmented plastic, black or pigmented cellulose, a chemical agent or any other absorbing or reflecting material known in the art, or just partially comprised of such a material to absorb or block signal generated by washed label and other interferents from outside the read area and thus prevent this background from moving back into the read area.

Alternatively, and with reference to FIG. 2, light absorbing or reflecting means can comprise an opaque, light blocking flange or the like, which is positioned between the absorbent material and the read area, and preferably, adjacent to the periphery of the read area. The flange is preferably comprised of at least one of the light absorbing or reflecting materials previously mentioned, or any other material known in the art, to absorb or block signal generated by washed label and other interferents from outside the read area prior to it re-entering the read area. When using the flange, it is understood that the absorbent material can also be comprised of a light absorbing or reflecting material as previously described. It is apparent that whatever embodiment or combination thereof which absorbent material/light absorbing or reflecting means comprises, it is understood that the light absorbing or reflecting material is to be included in the element in a manner to absorb or block signal generated by washed label and other interferents from outside the read area prior to it moving back into the read area.

Upon completion of the immunochemical reaction and absorption of the unbound label and serum components by the absorbent from within the read area, the read area is monitored with the aid of an appropriate instrument to determine the magnitude of the signal generated by the labeled compound. The read area (generally 6–12 mm in diameter) is confined to the portion of matrix within which the entrapped analyte and bound labeled compounds are present. The type of instrumentation employed will, of course, depend upon the type of immunoassay performed and the label used. As previously stated, and describe elsewhere herein, any label and detection method known in the art may be used.

The present invention is further illustrated by the following examples:

EXAMPLE I

Residual HRP Remaining In Read Area After Wash Procedures

Horseradish peroxidase (HRP), an enzyme commonly used as a label in immunoassays, may be washed away to background in thin-film immunoassay using the analytical element of the present invention with a large volume wash but not by using a conventional wash format volume. A sensitive chemiluminescent detection chemistry based on recrystalized luminol, hydrogen peroxide, and 4'-hydroxyacetanilide was used to detect remaining HRP. Buffer solution 1 contained 0.1 M tris(hydroxymethyl)-aminomethane (Tris), pH 8, $10^{-5}$ M diethylenetriaminepentacetic acid (DTPA), and 0.1% cetyltrimethylammonium-bromide (CTAB). A chemiluminescent reaction mixture (4×) was made by combining 4 mM recrystalized luminol, 600 $\mu$M 4'HA and 8 mM H2O2 to buffer solution 1. All measurements were made on an instrument which automates spotting of a 10 $\mu$L sample. This instrument automates spotting of a 10 $\mu$L sample, performs a 10 or 20 $\mu$L wash, read (8 mm read area), and records the chemiluminescent signal of the thin film. The reagent matrix used contained a beaded spreading layer with no antibody or detection chemistry. The absorbent layer was a synthetic plastic sponge obtained from Excello Company.

Figure 5:
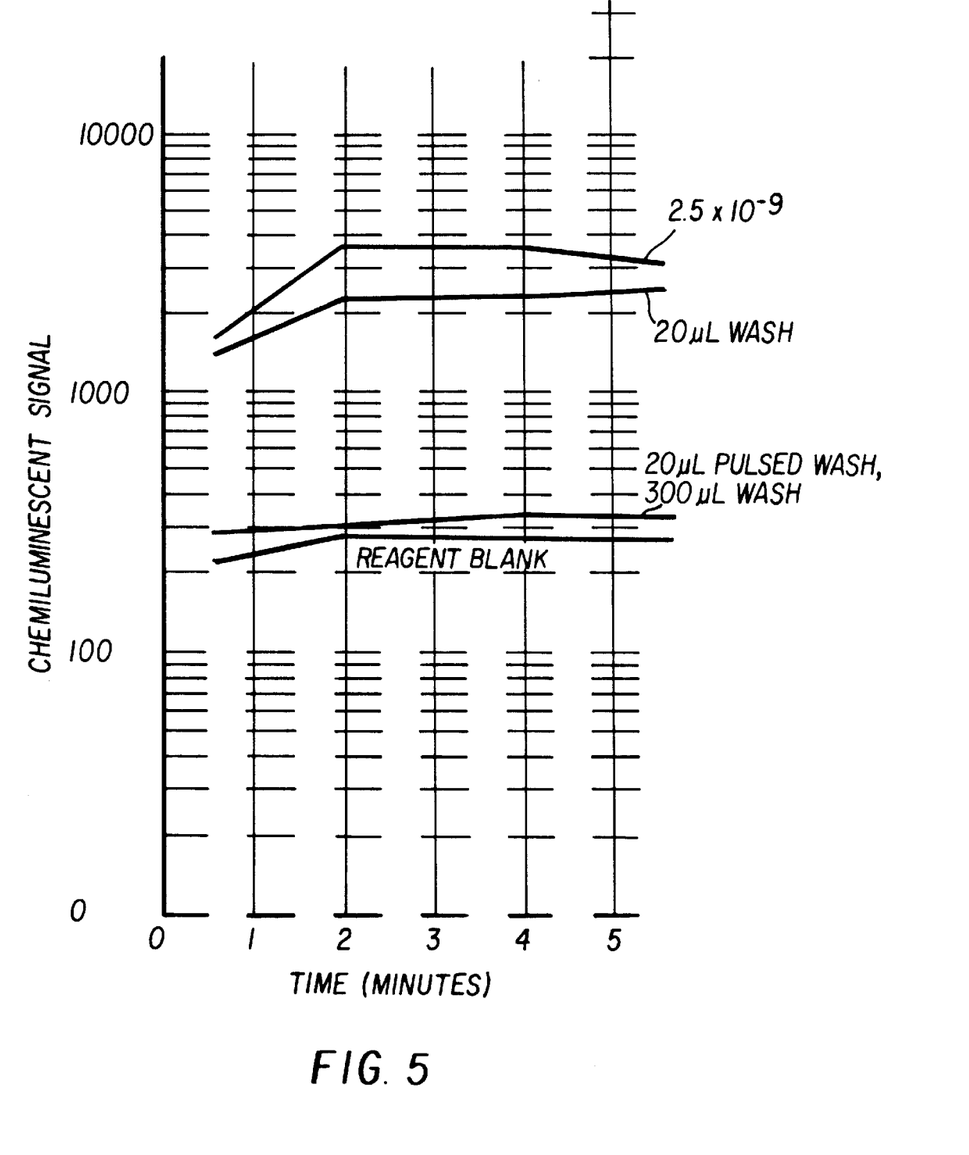
FIG. 5 illustrates chemiluminescent signal in logarithmic scale of HRP after wash procedure.

With reference to FIG. 5., for measurement of the signal in a reagent blank, 10 $\mu$L of a 1× dilution of chemiluminescent reagent was spotted on the reagent matrix, and chemiluminescence recorded. A positive reagent control (graph line, "2.5×10$^{-9}$ M HRP") shows the chemiluminescent signal from spotting 2.5×10$^{-9}$ M HRP in signal reagent on the matrix. 100 $\mu$L of 4× chemiluminescent reaction mixture, 300 $\mu$L of buffer solution 1, and 10 $\mu$L of a 1×10$^{-7}$ M HRP (2.5×10$^{-9}$ M HRP final concentration) were mixed in an Eppendorf tube prior to spotting. For the line in the graph labeled "20 $\mu$L wash," 10 $\mu$L of 2.5×10$^{-9}$ M HRP solution in chemiluminescent reaction mixture, prepared as above, was spotted on the matrix, followed by a 20 $\mu$L pulsed wash of 1× chemiluminescent reaction mixture. In the graph line labeled "20 $\mu$L pulsed wash, 300 $\mu$L wash," 10 $\mu$L of a 2.5×10$^{-9}$ M HRP solution in chemiluminescent reaction mixture was spotted on the reaction matrix, followed by a 20 $\mu$L pulsed wash with 1× chemiluminescent reaction mixture. An absorbent sponge, which had been previously sealed with hot paraffin around its periphery, was then placed around, and in intimate contact with, the read area of the element, and 10–20 $\mu$L pulsed washes of 1× chemiluminescent reagent manually dispensed with a pipette for a total of 300 $\mu$L were added.

Figure 6:
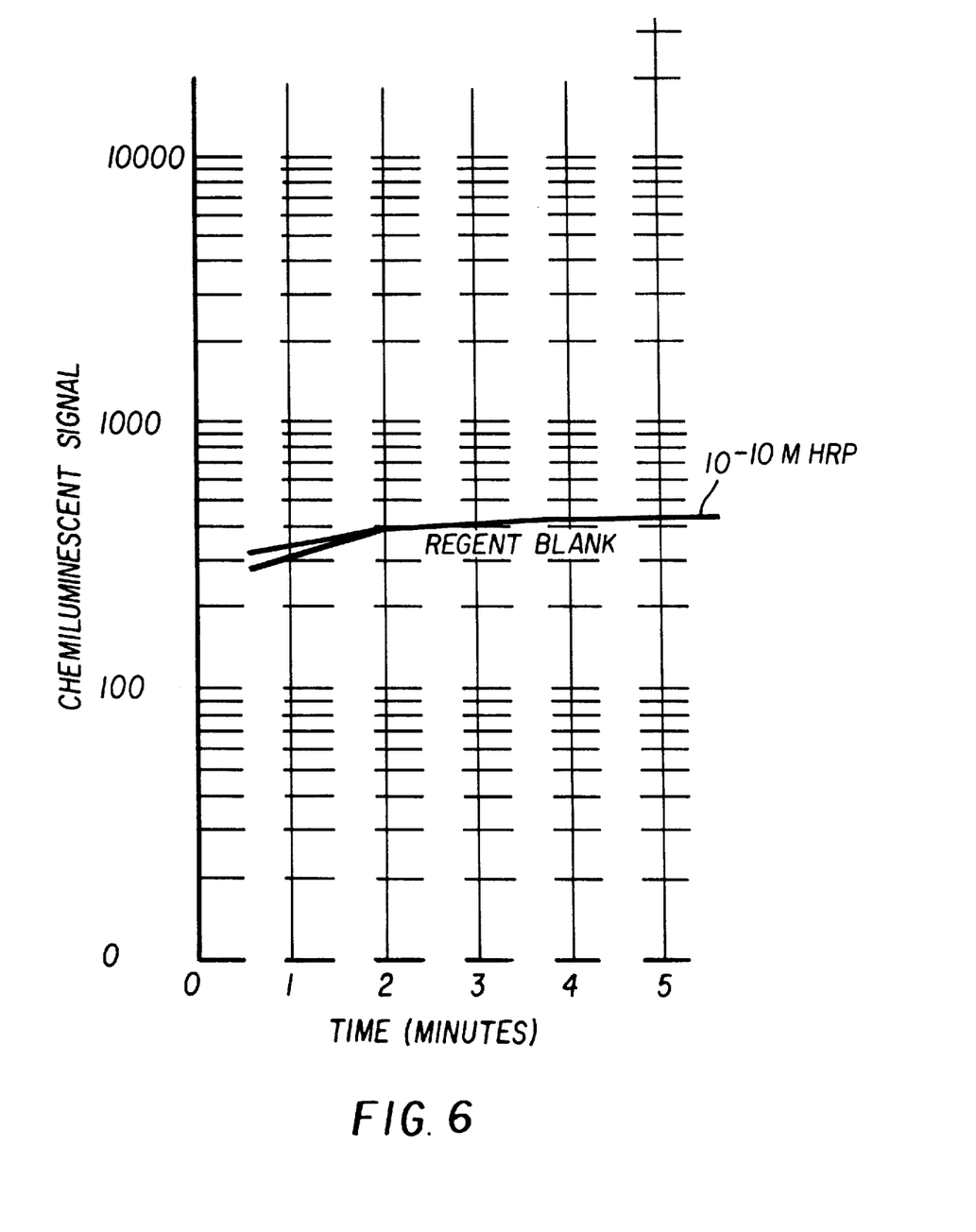
FIG. 6 illustrates chemiluminescent signal in logarithmic scale of HRP after wash procedure.

As shown in FIG. 5, in which chemiluminescent signal is presented in logarithmic scale, there is a very large HRP signal even when a 20 $\mu$L wash is used. In contrast, in increasing wash volume using the element of the present invention, background is reduced to virtually a level observed with the chemiluminescent reagents alone. With reference to FIG. 6, a repeat of the above experiment using the element of the invention is shown. In this experiment, background is also reduced to a level observed with chemiluminescent reagents alone.

EXAMPLE II

Evaluation of Washout of Horseradish Peroxidase (HRP)

Figure 7:
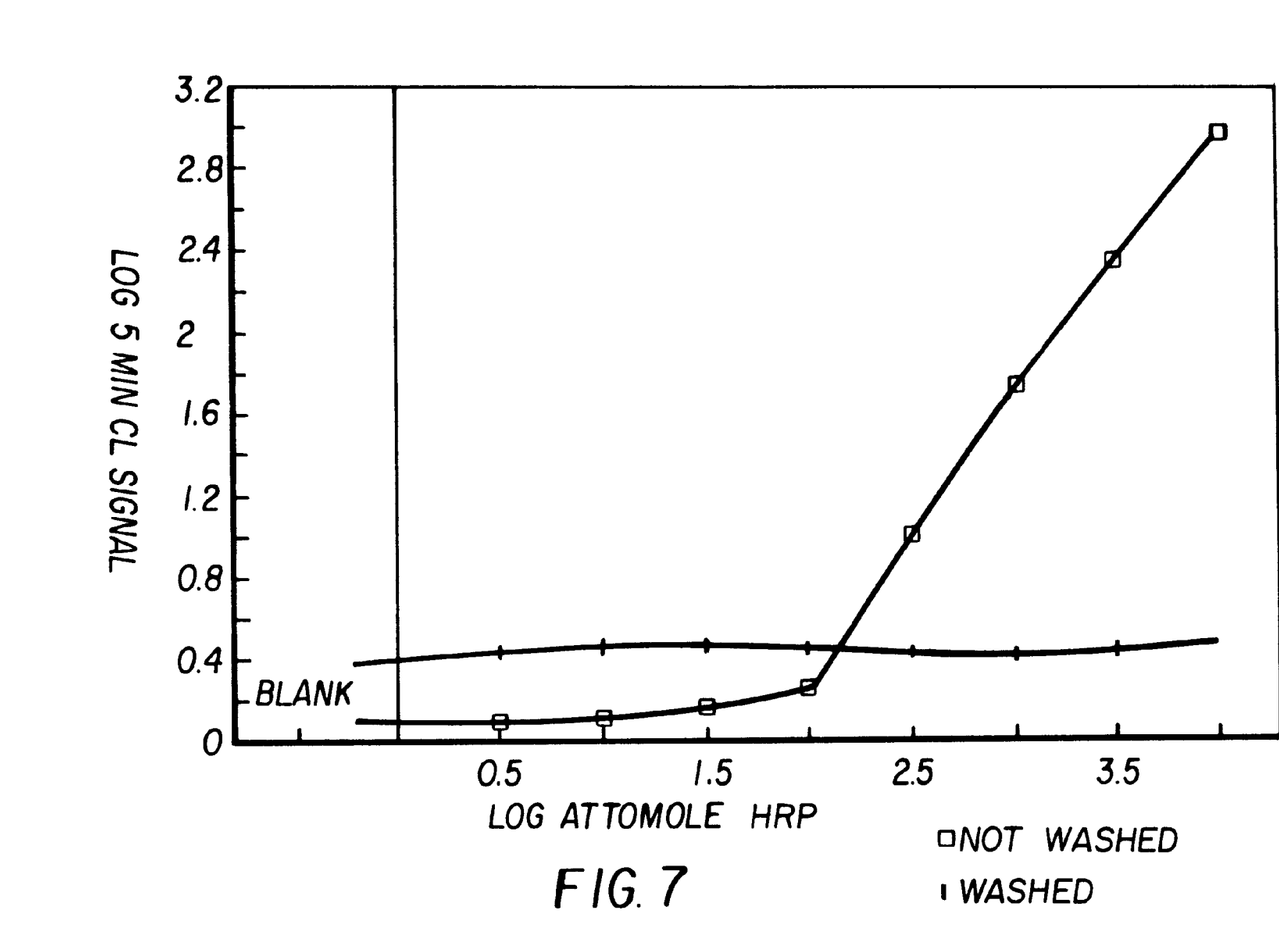
FIG. 7 illustrates a graph showing effect of 100 $\mu$L wash at 0.628 $\mu$L/sec on 10,000 attomoles of HRP.

This is an example of washout of HRP which is commonly used as an enzyme label in immunoassays. 0, 10, 100, 1000 and 10,000 attomoles of HRP in 10 $\mu$L buffer (0.1M tris, pH 8) were spotted on the reagent matrix comprised as shown in Table 1. The absorbent material was a GF/B absorbent provided by Whatman. 100 $\mu$L wash including signal reagent (Tris (0.1M, pH 8.0), luminol (1 mM), 4'HA (150 $\mu$M), H$_2$O$_2$ (2 mM), DTPA(10 $\mu$M) and CTAB(0.1%)) was dispensed by a wash station containing a metering pump at 0.63 $\mu$L/sec. Wash time was approximately 160 seconds. After the wash was complete, the reagent matrix, after removal from the support base, was read on a Turner luminometer TD20E, for 5 minutes at 37° C. for chemiluminescence. With reference to FIG. 7, 10,000 attomoles of HRP was washed to between background and 100 attomoles HRP with this method (detection limit of this reagent coating) and no cratering or wrinkling of reagent matrix was observed after 100 $\mu$L wash.

TABLE 1

| Reagent Matrix | |
| --- | --- |
| Bead spread layer | 0.1 M Tris, pH 8.0 |
| | Polymeric beads |
| | Binder |
| | Zonyl FSN |
| | Methanol |
| Gel pad | Gelatin |
| | 0.2 M Tris, pH 8.0 |
| | TX-100 |

The following definitions apply to the above reagent matrix:

Tris: Tris(hydroxymethyl)amino-methane buffer.

Polymeric beads: Poly(vinyltoluene-co-methacrylic acid beads).

Binder: Poly(methyl acrylate-co-sodium 2-acrylamido-2-methyl-propanesulfonate-co-2-acetoacetoxy-ethyl methacrylate).

Zonyl FSN: fluorinated surfactant sold by duPont de Nemours.

TX-100: Triton X-100, an octylphenoxy polyethoxy ethanol surfactant sold by Rohm and Haas Co.

EXAMPLE III

Washout Of 10.000 Attomoles Of HRP In Serum

Figure 8:
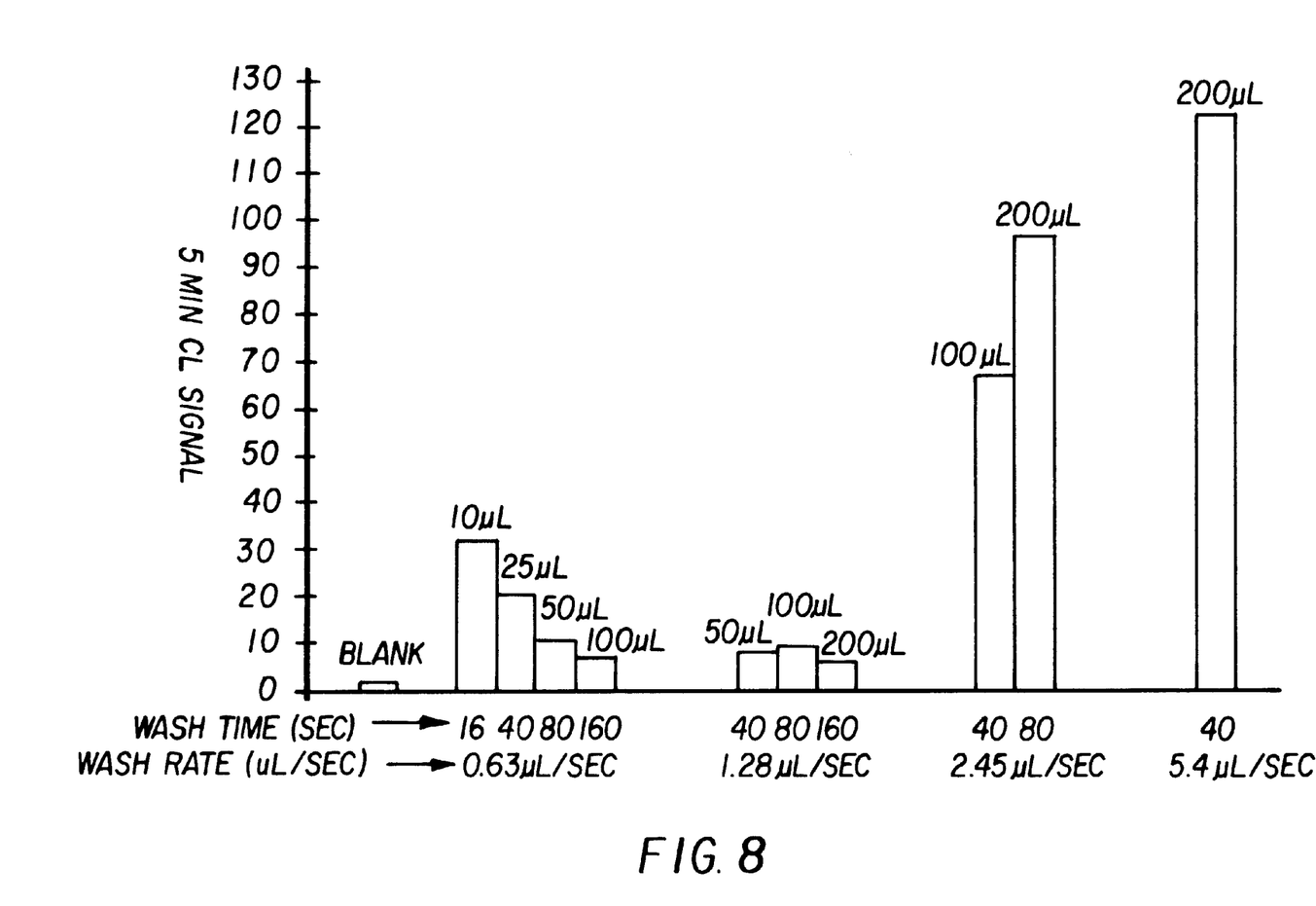
FIG. 8 illustrates a graph showing effect of wash rate and volume on 10,000 attomoles of HRP/serum.
Figure 9:
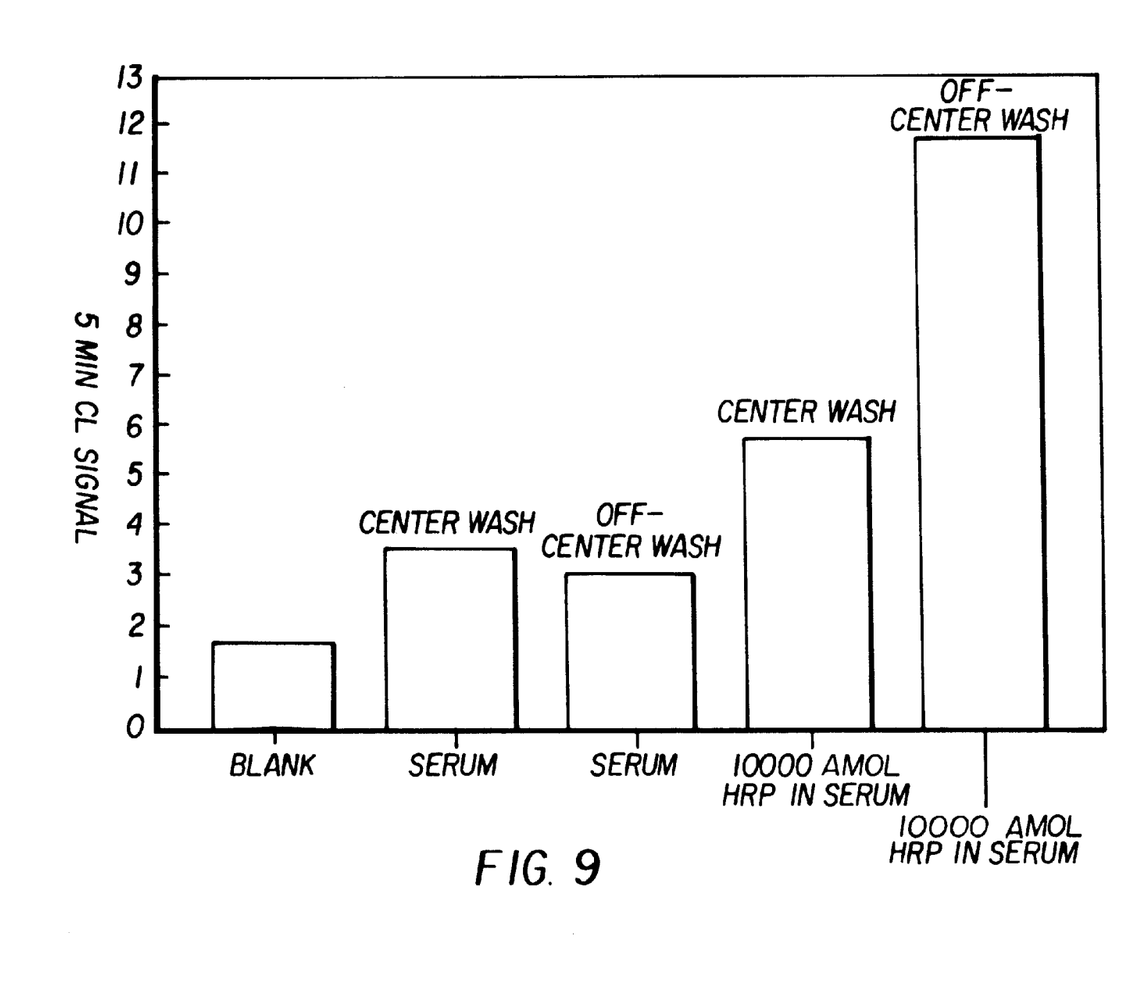
FIG. 9 illustrates a graph comparing effects of off center wash on chemiluminescent signal.

The analytical element was prepared as described in Example 2, except that 10,000 attomoles of HRP were used in the test sample. The results for specified wash times and rates are shown in FIG. 8. It has been shown that 10,000 attomoles HRP in serum can be washed to 3x background. Washout with 50 µL volume at rate of 1.28 µL/sec (40 second wash time) was optimum for this coated element.

EXAMPLE IV

Paraffin Seal

The analytical element was prepared as described in Example 2, except that a paraffin seal was applied to the edge of the absorbent layer, around the read area and upper slide mount to determine whether the presence of the paraffin improves the wash using 100 or 200 µL of wash fluid at a rate of 2.45 µL/sec (test serum sample=10 µL containing 10,000 attomoles of HRP) in comparison to controls having no paraffin seal. Melted paraffin was applied with a cotton tipped applicator stick. This experiment was performed because it was found that if the wash is applied all at once to a slide with no seal, the absorbent takes up fresh wash solution through the edge before it has a chance to perform the washing. It was further found that this could be prevented by applying the wax seal as described. Thus, the purpose of this experiment was to determine if adequate washing can be attained without the wax seal by using pulse washing over a longer time period rather than by flooding the slide with a single pulse of the total wash volume. The results are shown in Table II as follows:

TABLE II

| | | 5 min Signal*RCL of Washed Matrix | |
| --- | --- | --- | --- |
| Wash Volume | Wash Rate | Without Paraffin | With Paraffin |
| 100 µL | 2.45 µL/sec | 68 | 103, 108 |
| 200 µL | 2.45 µL/sec | 89, 106 | 145, 165 |

*RCL — relative chemiluminescence units

The paraffin seal appears not to significantly improve washing and thus is optional when such pulse washing is employed. However, in other experiments, it has been demonstrated that a paraffin seal is desired when a manually applied dropped wash is used.

EXAMPLE V

Effect of Varying Wash Volume in Removing HRP

This experiment examined the effect of varying wash volumes in removing HRP in an element in accordance with the invention having a reagent matrix with the format as shown in Table III:

TABLE III

| Bead Spread Layer: | 0.1 M Tris, pH 8.0 |
| --- | --- |
| | Polymeric beads |
| | Binder |
| | Zonyl FSN |
| | Methanol |
| Gel Pad: | Gelatin |
| | 0.2 M Tris, pH 8.0 |
| | TX-100 |

The following definitions apply to the above reagent matrix:

Tris: Tris(hydroxymethyl)amino-methane buffer.

Polymeric beads: Poly(vinyltoluene-co-methacrylic acid beads).

Binder: Poly(methyl acrylate-co-sodium 2-acrylamido-2-methylpropanesulfonate-co-2-acetoacetoxy-ethyl methacrylate).

Zonyl FSN: fluorinated surfactant sold by duPont de Nemours.

TX-100: Triton X-100, an octylphenoxy polyethoxy ethanol surfactant sold by Rohm and Haas Co.

10 µL of goat serum containing 10,000 attomoles of Horseradish peroxidase (HRP) was spotted on the above reagent matrix, which was mounted in a slide mount format containing a Whatman GF/B absorbent. The slide was incubated for 5 minutes at 37° C., then washed with luminol/electron transfer agent/$H_2O_2$ wash fluid/signal reagent. A wash rate of 0.8 µL/sec and wash volumes of either 10, 50, 75, 100 or 150 uL were used. The reagent matrix was removed from the slide mount and read on a Turner Lulinometer, Model TD20E, at 37° C. for 5 minutes.

Figure 10:
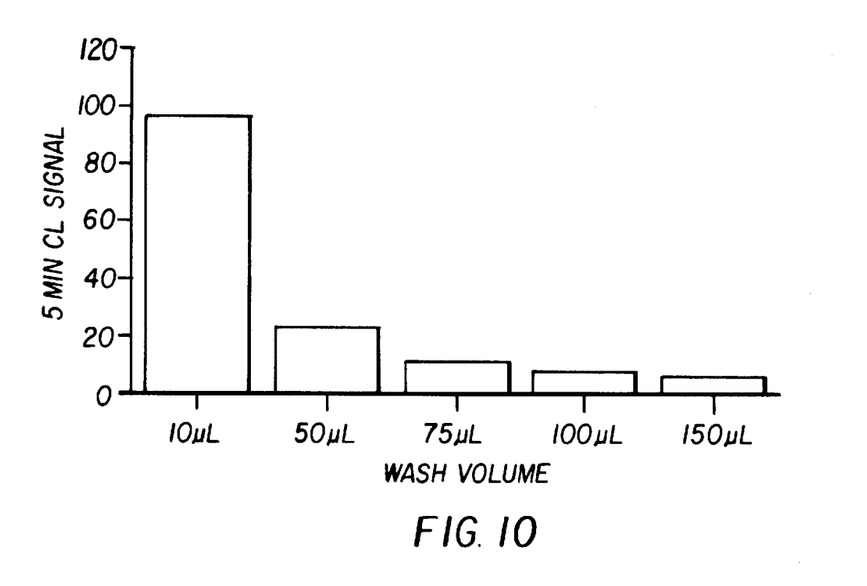
FIG. 10 illustrates a graph showing effects of wash rate and volume on 10,000 attomoles of HRP/serum.

Results of duplicate determinations for each value are shown in FIG. 10. The results suggest that HRP removal in the coating was improved with increased wash volume. The element used in this experiment accommodated up to 250 µL of wash fluid, wherein only 10–20 µL of wash fluid could be accommodated by the reagent matrix alone i.e., conventional format without absorbent.

EXAMPLE VI

The Use of a Black Flange and/or Black Absorbent to Reduce Light-piping of Signal from Absorbent Containing Removed Horseradish Peroxidase In the previous examples, the absorbent containing washed horseradish peroxidase (HRP) was not present during the chemiluminescent measurement since the coated element was removed from the slide mount prior to reading. In the present experiment, a luminometer was modified so that the intact slide, with the absorbent in place, could be read.

10 μL of serum containing 10,000 attomoles of HRP was spotted on a white slide mount/white absorbent format. The slide was incubated for 5 minutes at 37° C., then washed with 75 μL of luminol/electron transfer agent/H202 signal reagent/wash solution at 1 μL/sec. As shown in Format 1, Table IV, a signal of 56,509 relative chemiluminescent (RCL) units was obtained when the slide was read with the absorbent present. However, when the absorbent was removed prior to reading, a signal of 4811 RCL units was measured.

The following experiment was performed to verify that this difference in signal might be due to light-piping from washed HRP present in the absorbent. As shown in Table IV, several different combinations of light absorbing mounts and absorbents, as well as a mount designed with a light blocking flange, were evaluated for light-piping. Each slide was spotted, incubated and washed as described above, then read on the luminometer with and without the absorbent present.

Results of duplicate determinations are shown in Table IV which demonstrate that the presence of a black slide mount and/or black absorbent was effective in eliminating light-piping caused by washed HRP in the absorbent.

TABVLE IV

Relative Chemiluminescence Units

| Format[a] | Slide Mount | Absorbent | Absorbent Present for Read | Absorbent Removed for Read |
|---|---|---|---|---|
| 1 | white | white[b] | 56509 | 4811 |
| 2 | white | black[c] | 4756 | 4731 |
| 3 | white painted black | black[c] | 3980 | 3845 |
| 4 | black with flange | white[b] | 3415 | 2869 |
| 5 | black with flange | black[c] | 3087 | 3344 |

[a]See Table III for reagent matrix formats
[b]Whatman GF/B glass microfiber filter
[c]Schleicher and Schuell grade #508 filter, impregnated with activated carbon The invention has been described in detail with particular reference to certain preferred embodiments thereof, but it will be understood that variations and modifications can be effected within the spirit and scope of the invention.

EXAMPLE VII

Thin Film Immunoassay for Picomolar Analyte

This experiment demonstrated a workable immunoassay which can detect picomolar concentrations of an analyte using the element of the invention and chemiluminescent detection. A model coating to detect human chorionic gonadotropin (hcG) was used. The reagent matrix has the format as shown in Table V below:

TABLE V

| Spreading Layer | 0.1 M Tris, pH 8.0 |
| | Polymeric Bead |
| | Latex bead with immobilized antibody |
| | DTPA |
| | Binder |
| | Zonyl FSN |
| | Methanol |
| Gel Pad | Gelatin |
| | 0.2 M Tris, pH 8.0 |
| | TX-100 | wherein the following definitions apply to the reagent matrix:

DTPA: Diethylenetriaminepentaacetic acid, a chelator sold by Sigma Chemical Co.

Tris: Tris(hydroxymethyl) amino-methane buffer.

Polymeric beads: Poly(vinyltolvene-co-methacrylic acid beads).

Binder: Poly(methyl acrylate-co-sodium-2-acrylamido-2-methylpropanesulfonate-co-2-aceto-acetoxy-ethyl methacrylate).

Zongl FSN: Fluorinated surfactant sold by dePont de Nemours.

Figure 11:
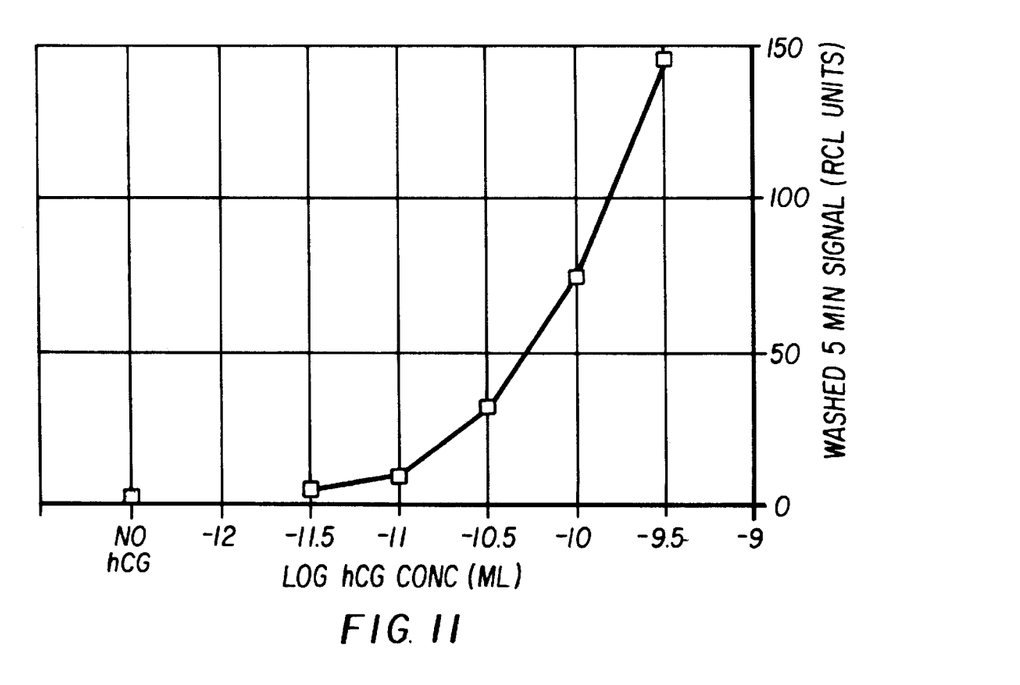
FIG. 11 is a graph illustrating results of an hcG assay using chemiluminescent detection.

TX-100: Triton X-100, an octylphenoxy polyethoxy ethanol surfactant sold by Rohm and Haas Co.

hcG was obtained from Sigma Chemical Co. The antibody-HRP conjugate was prepared by a modified method as described by Yoshitake et al., 1979, Eur. J. Biochem., Vol 101, pp. 395–399, which disclosure is hereby incorporated by reference. The element used was as shown in FIG. 1, and contained a Whatman GF/B absorbent. The hcG and antibody-HRP conjugate were mixed and incubated in 7% bovine serum albumin/phosphate buffered saline for 1 to 3 hours before spotting 10 μl on the reagent matrix of the element. Incubation, wash and read procedures were performed according to Example V. Wash volume and rate were 75 μl and 1 μl/sec., respectively. With reference to FIG. 11, the results show that using the element of the present invention it was possible to detect picomolar concentrations of hcG in thin film format.

We claim:

1. A dry analytical element for determination of an analyte in a fluid sample in thin film immunoassay comprising;
    (a) a support matrix;
    (b) a reagent matrix comprised of at least one layer of a porous material carried by said support member, said matrix comprising a read area;
    (c) a separate layer of an absorbent that
        (i) is in contact with the reagent matrix;
        (ii) is positioned adjacent to the periphery if the reagent matrix read area;
        (iii) absorbs wash fluid that contains soluble interferents and unbound label away from said read area; and
        (iv) comprises a light absorbing or reflecting material capable of substantially absorbing or blocking background signal generated outside the read area by washed, unbound label and other interferents from entering the read area.

2. The element of claim 1, wherein said immunoassay is selected from the group consisting of chemiluminescence, fluorescence and colorimetry immunoassay.

3. The element of claim 1, wherein said element further comprises a cover positioned above said absorbent.

4. The element of claim 3, wherein said cover is comprised of a material selected from the group consisting of paper, metal foils, polystyrene, polyesters, polycarbonates, cellulose esters, polyolefins, copolymers of olefins, polystyrene, polyethylene and polypropylene.

5. The element of claim 1, wherein said absorbent is selected from the group consisting of glass microfibers, paper, sponge, fabric and plastic.

6. The element of claim 1, wherein said light absorbing or reflecting material is selected from the group consisting of a pigmented polyvinyl alcohol, black plastic, black cellulose, and activated carbon.

7. The element of claim 1, wherein said reagent matrix is a multilayer porous material.

8. The element of claim 7, wherein said multilayer porous material comprises multilayers selected from the group consisting of reagent zones, capture zones, registration zones, additional spreading zones, radiation-blocking or filter zones, subbing zones, gel zones and barrier zones.

9. The element of claim 1, wherein said support member is comprised of a material selected from the group consisting of paper, metal foils, polystyrene, polyesters, polycarbonates, cellulose esters, polyolefins, copolymers of olefins, polystyrene, polyethylene and polypropylene.

10. The element of claim 1, further comprising a water-impermeable material around the periphery of the absorbent, adjacent to the read area, wherein the water-impermeable material is capable of preventing fluid from entering the absorbent prior to permeating the reagent matrix.

11. The element of claim 1, wherein said absorbent has a wash volume capacity of up to about 1 mL.

12. The element of claim 11, wherein said absorbent has a wash volume capacity of about 250 microliters.

* * * * *